US012268890B2

(12) United States Patent
Bakalo et al.

(10) Patent No.: US 12,268,890 B2
(45) Date of Patent: Apr. 8, 2025

(54) METHODS AND SYSTEMS FOR TRANSDUCER ARRAY PLACEMENT AND SKIN SURFACE CONDITION AVOIDANCE

(71) Applicant: Novocure GmbH, Root (CH)

(72) Inventors: Oren Ben Zion Bakalo, Haifa (IL); Reuven Ruby Shamir, Haifa (IL)

(73) Assignee: Novocure GmbH, Root (CH)

( * ) Notice: Subject to any disclaimer, the term of this patent is extended or adjusted under 35 U.S.C. 154(b) by 396 days.

(21) Appl. No.: 17/487,276

(22) Filed: Sep. 28, 2021

(65) Prior Publication Data

US 2022/0096853 A1   Mar. 31, 2022

Related U.S. Application Data

(60) Provisional application No. 63/085,905, filed on Sep. 30, 2020.

(51) Int. Cl.
| | | |
|---|---|---|
| *A61N 1/40* | (2006.01) | |
| *A61B 34/10* | (2016.01) | |
| *G16H 50/50* | (2018.01) | |

(52) U.S. Cl.
CPC ............... *A61N 1/40* (2013.01); *G16H 50/50* (2018.01); *A61B 2034/105* (2016.02)

(58) Field of Classification Search
CPC ... A61B 34/10; A61B 34/20; A61B 2034/107; A61B 2034/2065; A61B 90/13; A61B 90/50; A61B 2017/00725; A61B 2090/363; A61B 2090/376; A61B 2560/0437; A61B 90/37; G06T 7/80; G06V 10/26; G06V 10/50; G06V 2201/03; G06V 10/24; G06V 10/761; G06V 20/647

See application file for complete search history.

(56) References Cited

U.S. PATENT DOCUMENTS

| | | |
|---|---|---|
| 7,565,205 B2 | 7/2009 | Palti |
| 10,188,851 B2 * | 1/2019 | Wenger ............. A61N 1/36025 |

(Continued)

FOREIGN PATENT DOCUMENTS

| | | |
|---|---|---|
| CN | 108348761 A | 7/2018 |
| CN | 110234394 A | 9/2019 |
| CN | 110291390 A | 9/2019 |

*Primary Examiner* — Santiago Garcia
(74) *Attorney, Agent, or Firm* — McCarter & English, LLP; Michael A. Sartori (57) ABSTRACT

A method for applying tumor treating fields, the method comprising: determining, based on two-dimensional (2D) image data associated with a portion of a subject's body, one or more landmarks and one or more skin surface conditions; determining a representation of the one or more landmarks and the one or more skin surface conditions in three-dimensional (3D) space; determining, based on the representation of the one or more landmarks and the one or more skin surface conditions in 3D space, a plurality of placement positions for one or more transducer arrays on the subject's body for applying tumor treating fields; determining, based on the one or more skin surface conditions in 3D space, one or more recommended placement positions of the plurality of placement positions for the one or more transducer arrays; and outputting an indication of the one or more recommended placement positions for the one or more transducer arrays.

20 Claims, 10 Drawing Sheets

(56) References Cited

U.S. PATENT DOCUMENTS

| | | | | |
|---|---|---|---|---|
| 2009/0306509 | A1* | 12/2009 | Pedersen | G01S 15/8936 |
| | | | | 600/446 |
| 2013/0296684 | A1* | 11/2013 | Miller | A61B 8/4281 |
| | | | | 600/407 |
| 2015/0227680 | A1* | 8/2015 | Mainkar | G06T 17/00 |
| | | | | 703/11 |
| 2018/0160933 | A1* | 6/2018 | Urman | A61N 1/0476 |
| 2019/0009111 | A1* | 1/2019 | Myhr | A61B 34/10 |
| 2019/0117956 | A1* | 4/2019 | Wenger | A61N 1/36002 |
| 2019/0314631 | A1* | 10/2019 | Wong | A61N 1/40 |
| 2020/0398084 | A1* | 12/2020 | Guha | A61K 45/06 |
| 2021/0093897 | A1* | 4/2021 | Zadicario | G01R 33/4804 |
| 2021/0220480 | A1* | 7/2021 | Peyman | A61P 35/04 |
| 2021/0282748 | A1* | 9/2021 | Stehle | A61B 8/4494 |
| 2022/0020494 | A1* | 1/2022 | Shin | G06N 3/084 |
| 2022/0110698 | A1* | 4/2022 | Tolkowsky | A61B 6/505 |
| 2022/0265343 | A1* | 8/2022 | Onik | A61B 18/1477 |
| 2022/0401066 | A1* | 12/2022 | Verbakel | A61B 8/4488 |

* cited by examiner

TA2:
Shift 2cm towards the bottom and 1cm towards the face

FIG. 5B

TA2:
Rotate 15 degree towards the face

METHODS AND SYSTEMS FOR TRANSDUCER ARRAY PLACEMENT AND SKIN SURFACE CONDITION AVOIDANCE

CROSS-REFERENCE TO RELATED APPLICATIONS

This application claims priority to U.S. Patent Application No. 63/085,905 filed on Sep. 30, 2020, which is incorporated herein by reference.

BACKGROUND

Tumor treating fields (TTFields) are low intensity alternating electric fields within the intermediate frequency range, which may be used to treat tumors as described in U.S. Pat. No. 7,565,205. TTFields are induced non-invasively into a region of interest by transducers placed on the patient's body and applying AC voltages between the transducers.

Conventionally, a first pair of transducers and a second pair of transducers are placed on the subject's body. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

SUMMARY

One aspect of the invention is directed to a method for determining placement positions for transducer arrays on a subject's body for applying tumor treating fields. The method comprises: determining, based on two-dimensional (2D) image data associated with a portion of a subject's body, one or more landmarks and one or more skin surface conditions; determining a representation of the one or more landmarks and the one or more skin surface conditions in three-dimensional (3D) space based on the one or more landmarks and one or more skin surface conditions determined from the 2D image data; determining, based on the representation of the one or more landmarks and the one or more skin surface conditions in 3D space, a plurality of placement positions for one or more transducer arrays on the subject's body for applying tumor treating fields; determining, based on the one or more skin surface conditions in 3D space, one or more recommended placement positions of the plurality of placement positions for the one or more transducer arrays; and outputting an indication of the one or more recommended placement positions for the one or more transducer arrays.

The above aspect of the invention is exemplary, and other aspects and variations of the invention will be apparent from the following detailed description of embodiments.

DESCRIPTION OF EMBODIMENTS

This application describes exemplary methods and system to determine locations of transducer arrays on a subject's body to avoid and/or prevent skin surface conditions. The application of TTFields treatment may cause one or more skin surface conditions. For example, if the placement of one or more transducer arrays is not routinely repositioned relative to a portion of a patient's body, then beneath-array surface conditions may occur at the routine placement site for the one or more transducer arrays.

Figure 1:
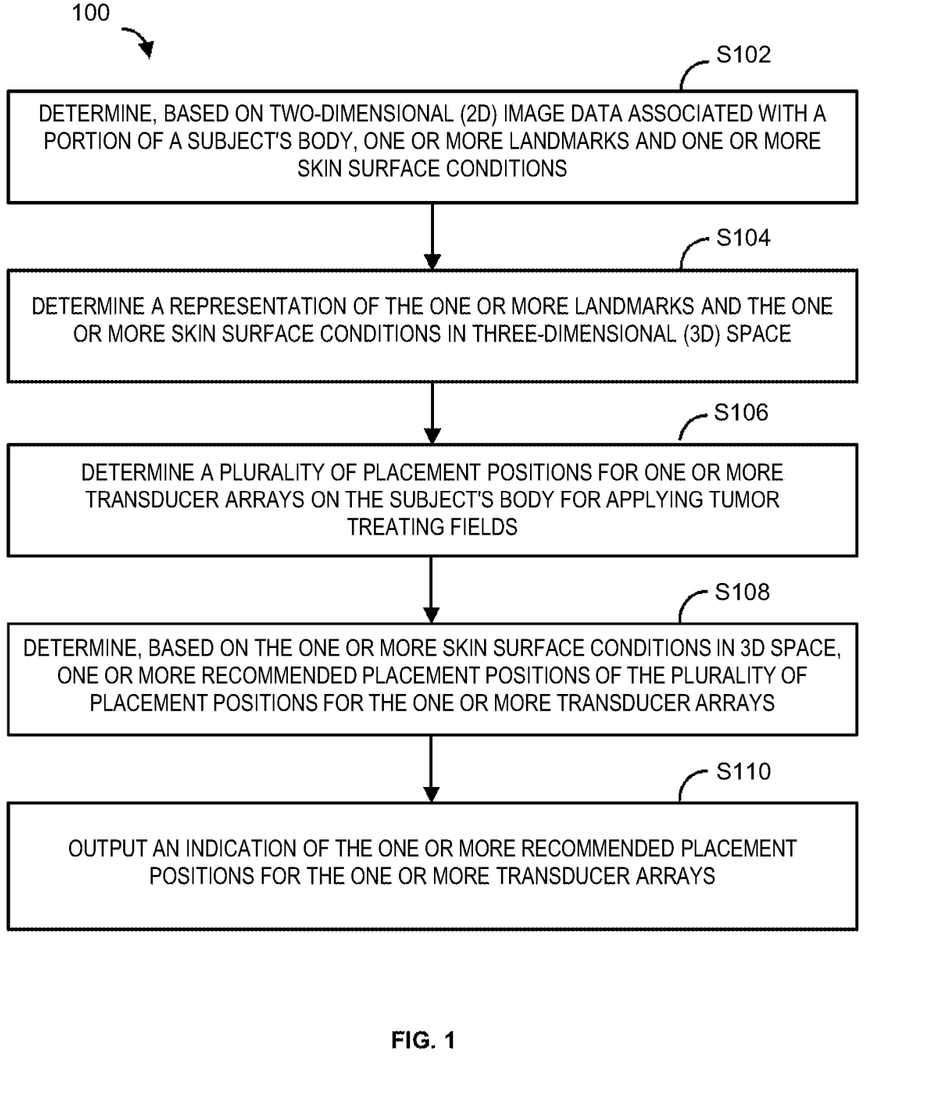
FIG. 1 is a flowchart depicting an example of determining placement positions for transducer arrays on a subject's body for applying TTFields.

FIG. 1 is a flowchart depicting an example method 100 of determining placement positions for transducer arrays on a subject's body for applying TTFields. With reference to FIG. 1, at step S102, the method 100 comprises determining, based on two-dimensional (2D) image data associated with a portion of a subject's body, one or more landmarks and one or more skin surface conditions. In some examples, the 2D image data may be a plurality of images obtained by a user device, e.g., a smartphone, a mobile device, or a computing device. In one example, each image of the plurality of images is associated with a different vantage point relative to the portion of the subject's body. In some examples, the portion of the subject's body is the head. In other examples, the portion of the subject's body is the torso. In one embodiment, the one or more landmarks and one or more skin surface conditions may be automatically determined via object recognition, machine learning, and/or the like. In another embodiment, the one or more landmarks and one or more skin surface conditions may be marked by a user in a user device.

In one example, the one or more landmarks comprise at least one of: an anatomical landmark, a sticker, or a temporary tattoo. As an example, the anatomical landmarks may include body locations, e.g., head, bones/ligaments, joints, and/or facial expression points (e.g., eyes, nose, eyebrows, etc.). In another example, the one or more skin surface conditions comprise at least one of: a skin irritation, a skin reaction, a scar tissue, a surgical site, or an area of medical device implantation. As an example, the one or more skin surface conditions may be beneath-array skin irritations, skin reactions, scar tissue, surgical sites, areas of medical device implantation (e.g., an Ommata reservoir, cranioplasty, or electrode implantation), and/or any other dermatologic occurrence. The beneath-array skin irritation may be a result of prolonged/extended TTFields treatment where the placement of transducer arrays has not been routinely repositioned. As an example, the beneath-array skin irritation may be a skin reaction, hyperhidrosis, xerosis, pruritus, skin erosion/ulcer, infection, and/or the like.

At step S104, the method 100 comprises determining a representation of the one or more landmarks and the one or more skin surface conditions in three-dimensional (3D)

space. Determining the representation of the one or more landmarks and the one or more skin surface conditions in 3D space may include applying a projection matrix to one or more 2D coordinates associated with the one or more landmarks and the one or more skin surface conditions.

At step S106, the method 100 comprises determining, based on the representation of the one or more landmarks and the one or more skin surface conditions in 3D space, a plurality of placement positions for one or more transducer arrays on the subject's body for applying TTFields. In one embodiment, the transducer array comprises a plurality of coupled electrodes. In another embodiment, the transducer array comprises a plurality of non-coupled electrodes. In one example, the transducer is a plurality of ceramic disks. In another example, the transducer is a polymer film.

In another embodiment, additional image data associated with the portion of the subject's body may be used to generate and/or determine 3D points and/or coordinates. As an example, the additional image data may comprise medical imaging data, e.g., magnetic resonance imaging (MRI) data, x-ray computed tomography (x-ray CT) data, single-photon emission computed tomography (SPECT) image data, and/or positron emission tomography (PET) data.

At step S108, the method 100 comprises determining, based on the one or more skin surface conditions in 3D space, one or more recommended placement positions of the plurality of placement positions for the one or more transducer arrays. In one embodiment, two of the recommended placement positions differ by at least one of the following: locations on the subject's body to place the one or more transducer arrays; sizes of electrodes of the one or more transducer arrays; shapes of the one or more transducer arrays; or orientations of the one or more transducer arrays. As an example, two of the recommended placement positions differ by the transducer array rotated by approximately 10 degrees to approximately 20 degrees around a centroid of the transducer array when compared to each other. As another example, at least one of the recommended placement positions comprises cutting away a portion of a bandage of one of the transducer arrays of the recommended placement position. As another example, at least one of the recommended placement positions comprises removing an electrode or part of an electrode of one of the transducer arrays of the recommended placement position. Examples of these embodiments regarding the recommended placement positions are illustrated in FIGS. 5A-5D, which is discussed further below.

In one embodiment, the one or more recommended placement positions may be determined based on an overlap with the one or more skin surface conditions. In one example, the one or more transducer arrays of the one or more recommended placement positions do not overlap with the one or more skin surface conditions. For example, each electrode of the one or more transducer arrays of the one or more recommended placement positions does not overlap with the one or more skin surface conditions. In another example, at least one electrode of the one or more transducer arrays of the one or more recommended placement positions partially overlaps with the one or more skin surface conditions. In this example, the method 100 may further comprise determining and outputting a percentage of overlap between the one or more skin surface conditions and each of the one or more transducer arrays of the one or more recommended placement positions.

In another embodiment, the one or more recommended placement positions may be determined further based on a calculated power density delivered to a tumor location in the subject's body for each of the plurality of placement positions. The power density of the TTFields may be used to represent the TTFields dose delivered to the corresponding region of interest, e.g., the tumor location.

In one embodiment, the method 100 may further comprise ranking the plurality of placement positions. In some examples, ranking the plurality of placement positions may be based on at least one of: a calculated power density delivered to a tumor location in the subject's body for each placement position; a percentage of overlap between the skin surface conditions and a bandage of each transducer array of each placement position; or a percentage of overlap between the skin surface conditions and each electrode of each transducer array of each placement position. As an example, the one or more recommended transducer placement positions may be determined (step S108) based on the ranking of the plurality of placement positions.

At step S110, the method 100 comprises outputting an indication of the one or more recommended placement positions for the one or more transducer arrays. In one embodiment, the indication of the one or more recommended placement positions is output to a user device. In some embodiments, the indications of the one or more recommended placement positions, the one or more landmarks, and/or the one or more skin surface conditions may be displayed (e.g., superimposed, overlaid, etc.) with an actual image and/or realistic depiction of a user and/or the portion of the user's body.

Figure 2:
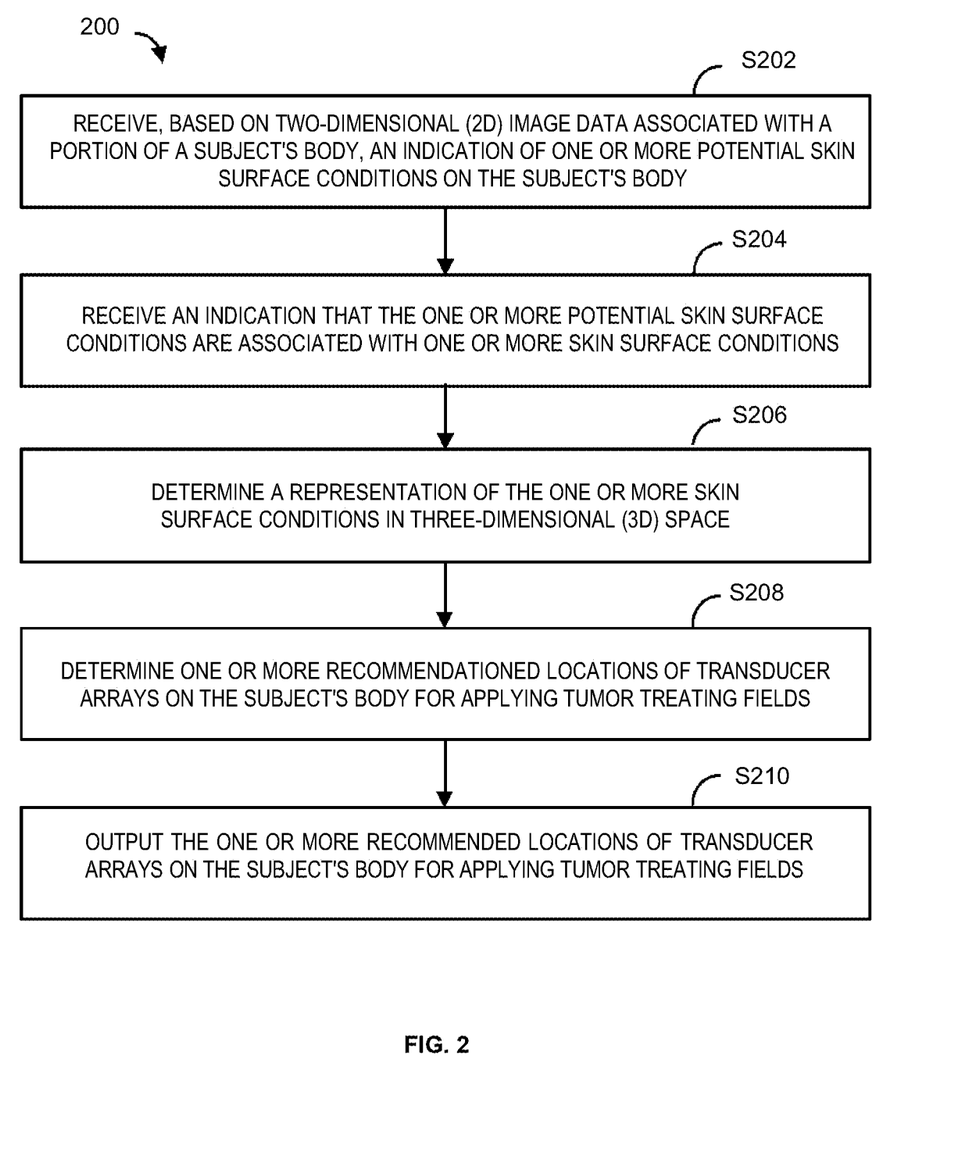
FIG. 2 is a flowchart depicting another example of determining locations of transducer arrays on a subject's body for applying TTFields.

FIG. 2 is a flowchart depicting an example method 200 of determining locations of transducer arrays on a subject's body for applying TTFields. With reference to FIG. 2, at step S202, the method 200 comprises receiving, based on 2D image data associated with a portion of a subject's body, an indication of one or more potential skin surface conditions on the subject's body. In one embodiment, the one or more potential skin surface conditions may be one or more of the skin surface conditions discussed at step S102.

At step S204, the method 200 comprises receiving an indication that the one or more potential skin surface conditions are associated with one or more skin surface conditions. In one embodiment, the indication that the one or more potential skin surface conditions are associated with one or more skin surface conditions may be determined based on object recognition.

At step S206, the method 200 comprises determining, based on the 2D image data received at S202 and the indication that the one or more potential skin surface conditions are associated with the one or more skin surface conditions determined at S204, a representation of the one or more skin surface conditions in three-dimensional (3D) space.

At step S208, the method 200 comprises determining, based on the representation of the one or more skin surface conditions in 3D space, one or more recommended locations of transducer arrays on the subject's body for applying TTFields. In one embodiment, the determination of the one or more recommended locations of the transducer arrays is further based on a transducer placement restriction. In one example, the transducer placement restriction restricts the one or more recommended locations based on an overlap of the transducer arrays with the one or more skin surface conditions. As a specific example, the transducer placement restriction includes a threshold of overlapping between the transducer arrays and the one or more skin surface conditions. For example, the transducer placement restriction may require 20% or less of overlapping between the transducer arrays and the one or more skin surface conditions.

At step S210, the method comprises outputting the one or more recommended locations of transducer arrays on the subject's body for applying TTFields to a user device. In one embodiment, the method further comprises generating and sending composite data to a user device. In one example, the composite data comprise a representation of the portion of the subject's body, a representation of at least one skin surface condition, and a representation of at least one recommended location of the transducer array.

Figure 3:
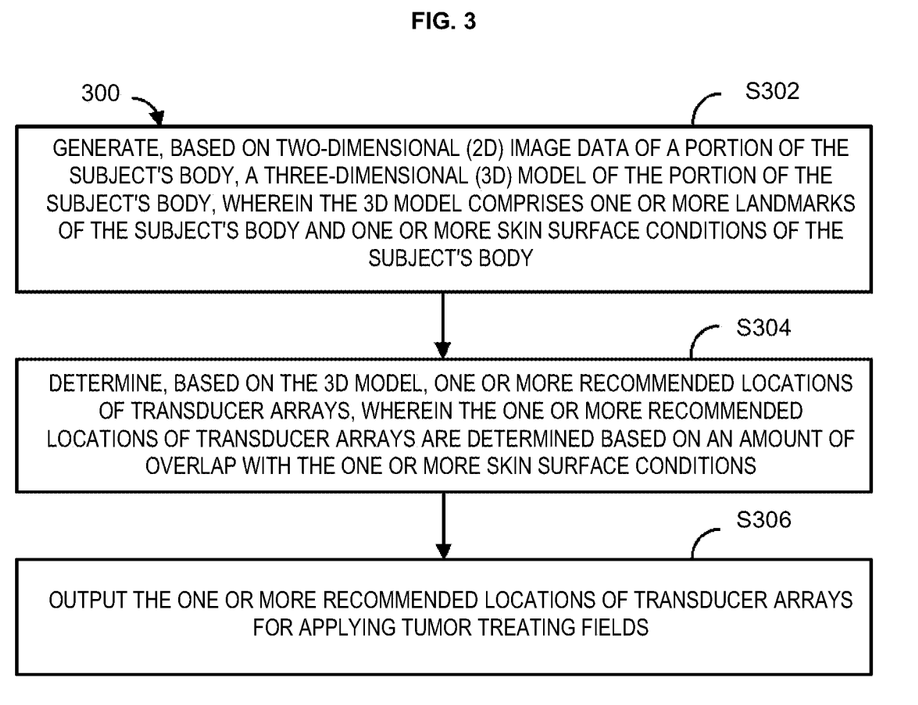
FIG. 3 is a flowchart depicting another example of determining locations of transducer arrays on a subject's body for applying TTFields.

FIG. 3 is a flowchart depicting an example method 300 of determining locations of transducer arrays on a subject's body for applying TTFields. With reference to FIG. 3, at step S302, the method 300 comprises generating, based on two-dimensional (2D) image data of a portion of the subject's body, a three-dimensional (3D) model of the portion of the subject's body. In one embodiment, the 3D model comprises one or more landmarks and one or more skin surface conditions of the subject's body.

At step S304, the method 300 comprises determining, based on the generated 3D model, one or more recommended locations of transducer arrays. In one embodiment, the one or more recommended locations of transducer arrays are determined based on an amount of overlap with the one or more skin surface conditions. In some embodiments, the method may further comprise ranking a plurality of locations of transducer arrays based on the overlapping between the transducer arrays and the one or more skin surface conditions. In this example, the one or more recommended locations of transducer arrays may be generated based on the ranking.

At step S306, the method 300 comprises outputting the one or more recommended locations of transducer arrays for applying tumor treating fields to a user device.

FIGS. 4A-4D depict an example system for determining locations of transducer arrays on a subject's body.

Figure 4A:
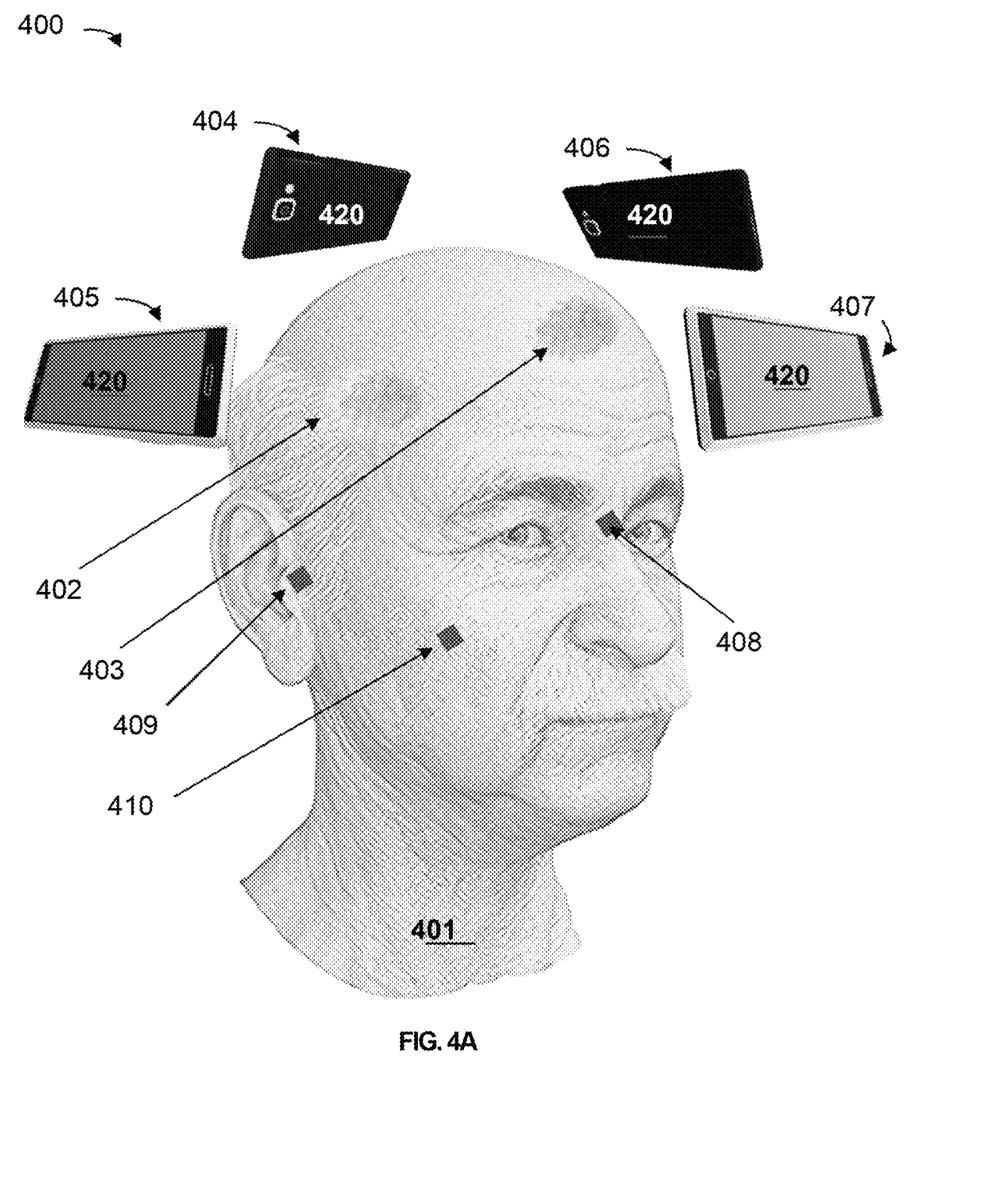
FIGS. 4A-4D depict an example system for determining locations of transducer arrays on a subject's body.

FIG. 4A depicts an example use of a user device 420 for determining and/or capturing 2D image data that may be used for transducer array placement and skin surface condition avoidance. In FIG. 4A, the user device 420 may capture a plurality of 2D images of a head portion of a user 401. The head of the user 401 may include one or more skin surface conditions 402 and 403 of skin irritation. The head of the user 401 may include one or more landmarks and/or tracking points, such as anatomical landmarks and/or visual/artificial landmarks. For example, anatomical landmark 408 may include the root of the nose, and anatomical landmark 409 may include the tragus of the ear. Landmark 410 may include an indicator (e.g., a sticker, a mark/temporary tattoo, an object, etc.) placed on a cheek of the user 401 so that the portion of the user's body may be determined/identified and correlated and/or associated with 3D image data (e.g., MRI image data, CT image data, medical image data, etc.) associated with the user.

To facilitate transducer array placement and skin surface condition avoidance, the user device 420 may capture a plurality of images of the user 401. The plurality of images may be taken from multiple vantage points, viewpoints, and/or the like. For example, the user device 420 may capture images from positions 404, 405, 406, and 407.

Figure 4B:
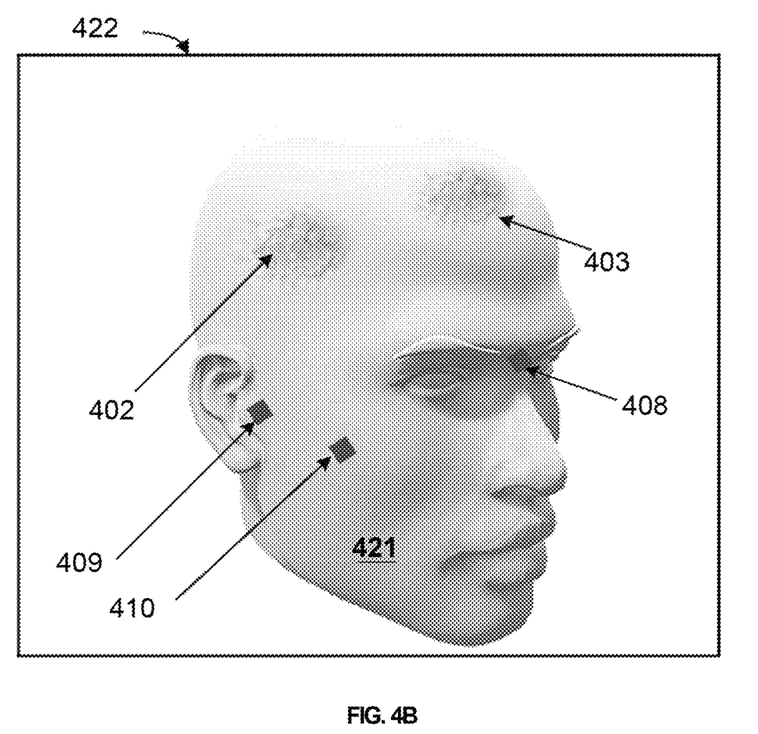

FIG. 4B shows an example representation of the user 401 of FIG. 4A in 3D space 422, based on image data from the user device 420. A 3D avatar 421 may represent the user 401. As shown, the indications of the landmarks 408, 409, and 410 and skin surface conditions 402 and 403 may also be represented in the 3D avatar 421. In some embodiments, representations and/or indications of the landmarks 408, 409, and 410 and skin surface conditions 402 and 403 may be displayed (e.g., superimposed, overlaid, etc.) with an actual image and/or realistic depiction of a user and/or the portion of the user's body.

Figure 4C:
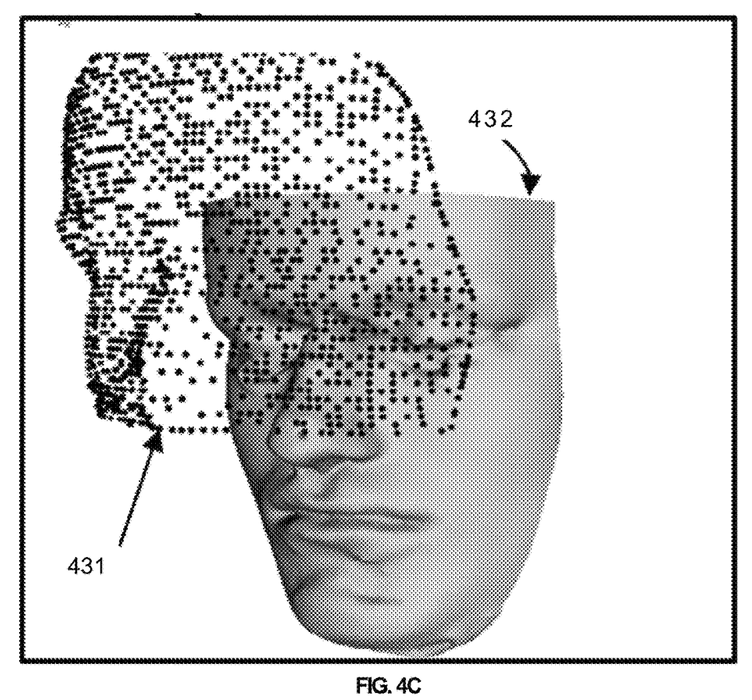
Figure 4D:
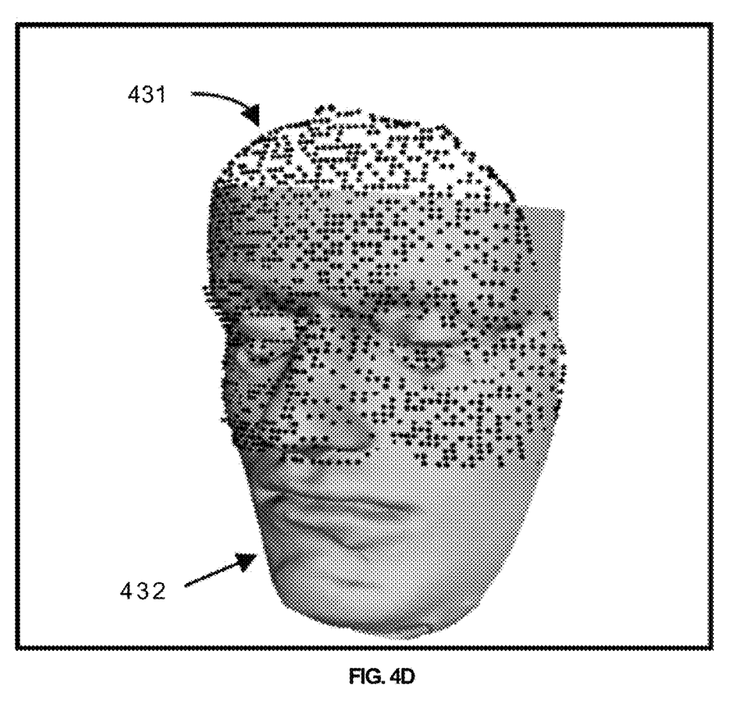

FIGS. 4C and 4D show an example representation of surface-based registration. The image data of the user 401 may be used to determine a plurality of points 431 (e.g., a dataset, etc.) indicative of a facial skin surface of the user 401. The surface 432 represents a skin surface extracted from 2D image data associated with the user 401. FIG. 4C shows the initial positions of the plurality of points 431. FIG. 4D shows the plurality of points 431 after they have been registered to the surface 432. Registration may be performed, for example, using an iterative closest point algorithm and/or the like.

FIGS. 5A-5D depict examples of visual notifications for transducer array placement.

Figure 5A:
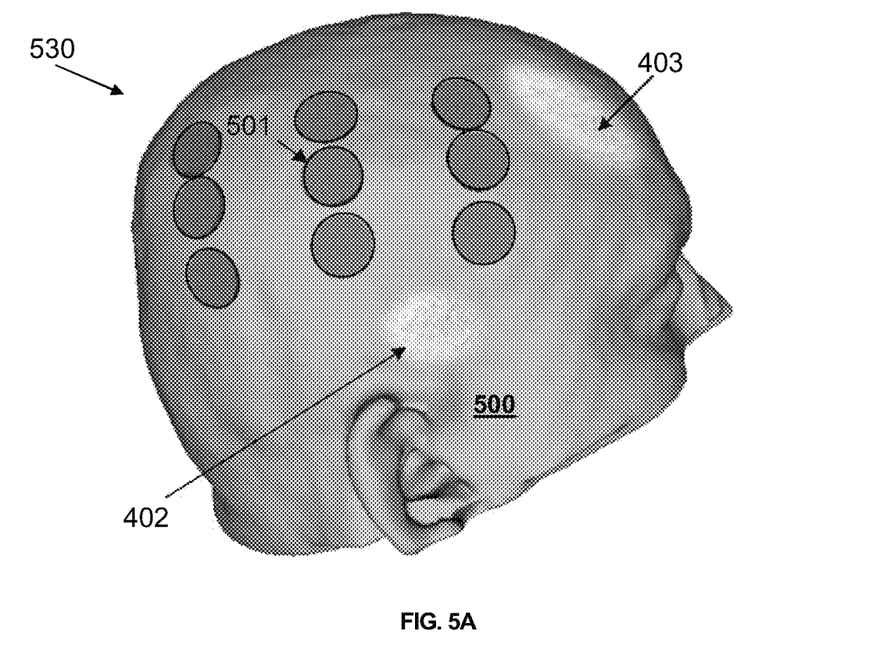
FIGS. 5A-5D depict examples of visual notifications for transducer array placement.

FIG. 5A depicts an example visual notification 530 that may be used for transducer array placement and skin surface condition avoidance. The one or more recommended placement positions for the one or more transducer arrays and the one or more skin surface conditions 402 and 403, may be displayed to the user. The one or more skin surface conditions 402 and 403 may be presented on a volumetric representation 500 of the user determined from 2D image data associated with the user, for example as a colored mesh and/or with more realistic texture. The one or more recommended placement positions for the one or more transducer arrays may be represented by gray circles 501. The notification may visually instruct the user where to place a transducer array to 1) avoid the one or more skin surface conditions and/or adhere to a transducer array placement restriction, and 2) receive an optimized electric field applied to a region of interest, such as a tumor site.

Figure 5B:
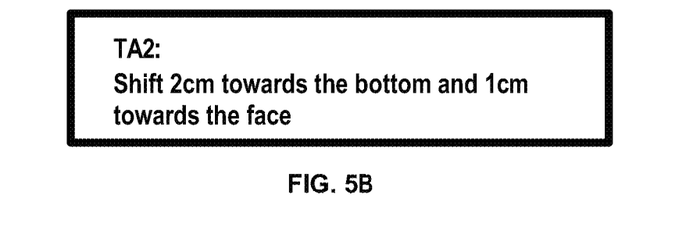
Figure 5C:
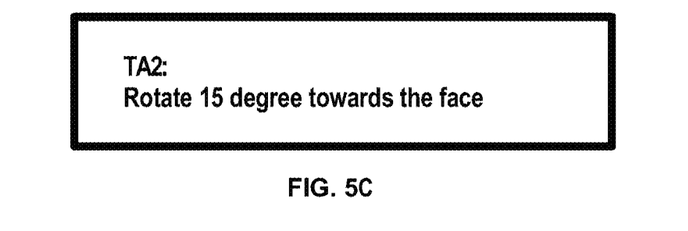

FIGS. 5B and 5C depict example notifications that may be used for transducer array placement. For example, object recognition may be used to determine the actual placement positions for one or more transducer arrays and compare the actual placement positions to the one or more recommended placement positions for the one or more transducer arrays. Based on the comparison, a variance is determined of at least one of the one or more placement positions from at least one of the recommended placement positions. To resolve/correct the variance, a notification may be sent to a user device, leading the user to reposition the locations/positions where the one or more transducer arrays are placed to match the one or more recommended placement positions. In the example depicted in FIG. 5B, a notification of "Shift 2 cm towards the bottom and 1 cm towards the face" is sent to a user device. In the example depicted in FIG. 5C, a notification of "Rotate 15 degree towards the face" is sent to a user device.

Figure 5D:
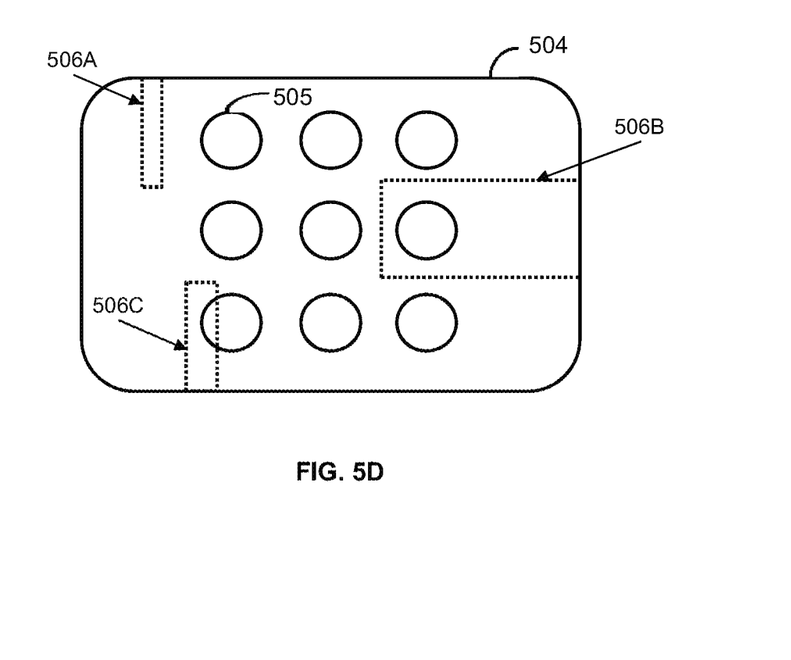

FIG. 5D depict a visual notification of adjusting the size or shape of the transducer array that may be sent to a user device for transducer array placement and skin surface condition avoidance. In the example depicted in FIG. 5D, the transducer array comprises a bandage 504 and a plurality of electrodes 505. As an example, the visual notification may include recommendations to cut away a portion of the bandage 504 (e.g., portion 506A). As another example, the visual notification may include recommendation to remove an electrode 505 (e.g., cutting away portion 506B) or to remove a part of an electrode 505 (e.g., cutting away portion 506C).

Figure 6:
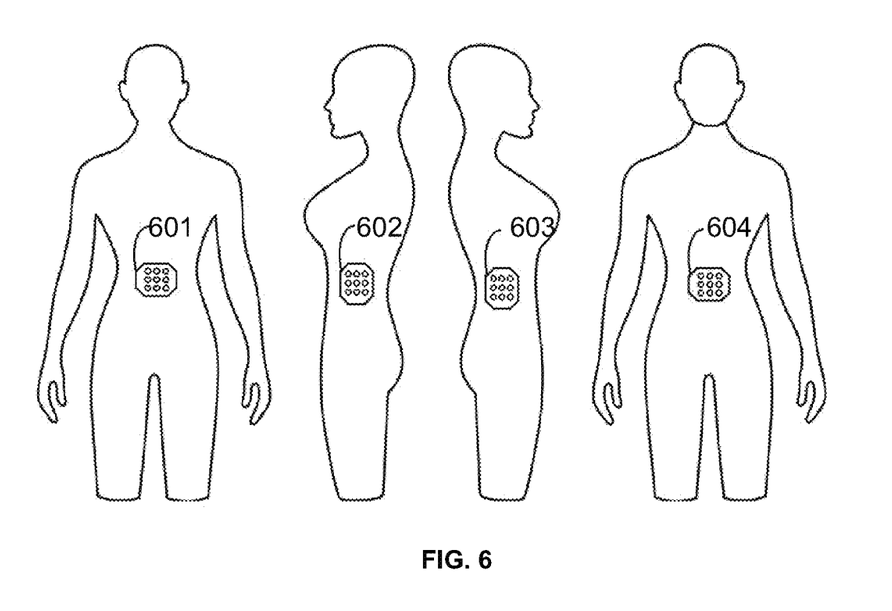
FIG. 6 depicts an example of transducer arrays placed on a subject's torso.

FIG. 6 depicts an example of transducer arrays placed on a subject's torso. In FIG. 6, the determination of the placements of transducer arrays 601, 602, 603, and 604 is similar to, for example, the process discussed in FIGS. 4A-4D and FIGS. 5A-5D above.

Figure 7:
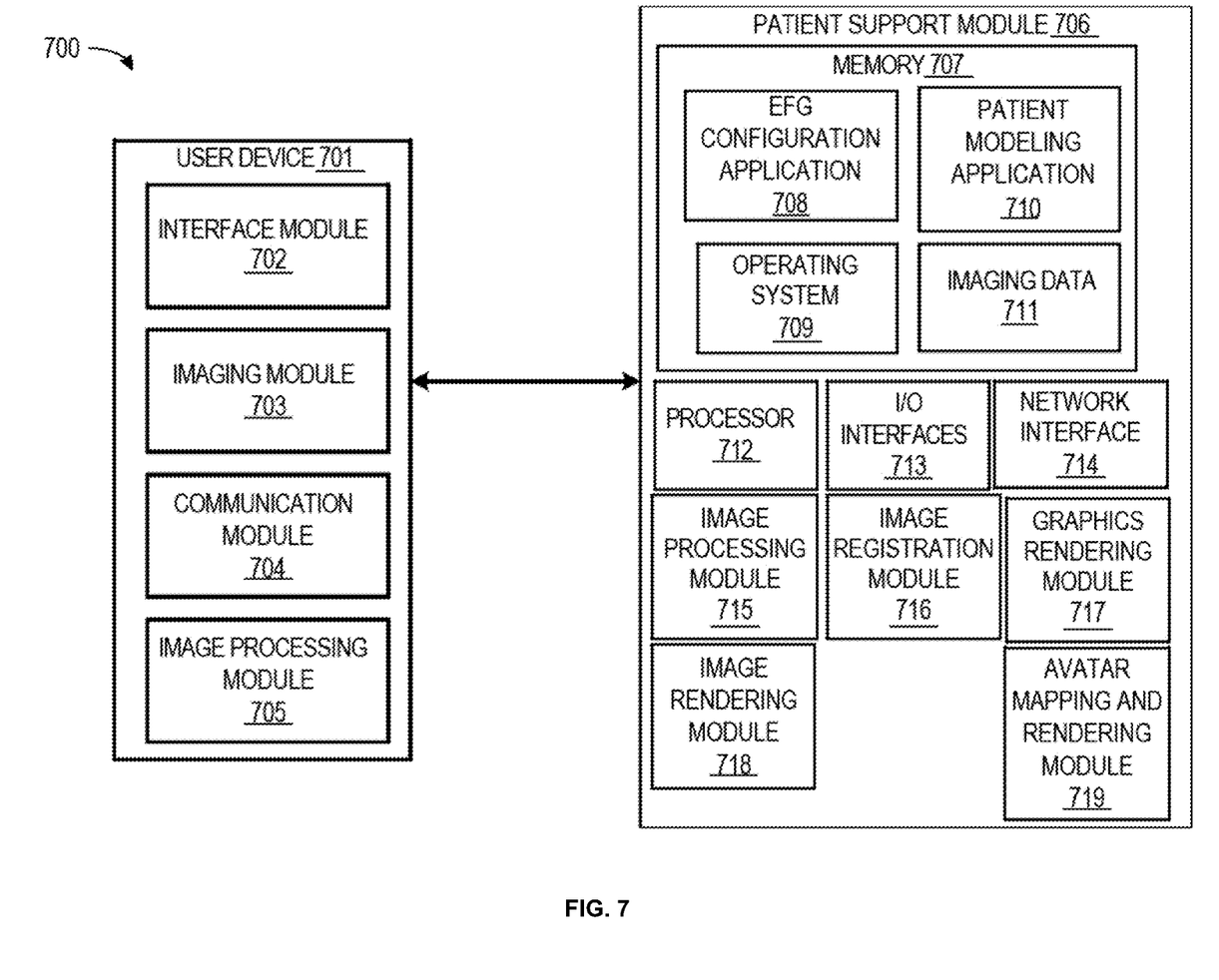
FIG. 7 depicts an example system for determining locations of transducer arrays.

FIG. 7 depicts an example system for determining locations of transducer arrays. In one embodiment, components of the system 700 may be implemented as a single device. In another embodiment, components of the system 700 may be implemented as separate devices/components in collective communication.

The system 700 may include a user device 701. The user device 701 may be an electronic device such as a smartphone, a mobile device, a computing device, and/or the like capable of communicating with a patient support module 706. The user device 701 may include an interface module 702. The interface module 702 may provide an interface for the user to interact with the user device 701 and/or the patient support module 706. The interface module 702 may include one or more interfaces for presenting and/or receiving information to/from the user, such data/information (e.g., 2D data/information, 3D data/information, etc.) indicative of one or more landmarks, one or more skin surface conditions, one or more recommended placement positions for transducer arrays, and/or adherence to a transducer array placement restriction. The interface module 702 may include one or more audio devices (e.g., stereos, speakers, microphones, etc.) for capturing/obtaining audio information and conveying audio information, such as audio information captured/obtained from the user and/or conveyed to the user. The interface module 702 may include a graphical user interface (GUI), a web browser (e.g., Internet Explorer®, Mozilla Firefox®, Google Chrome®, Safari®, or the like), or an application/API. The interface module 702 may request and/or query various files from a local source and/or a remote source, such as the patient support module 706. The interface module 702 may include one or more displays (e.g., monitors, liquid crystal displays, organic light-emitting diode displays, active-matrix organic light-emitting diode displays, stereo displays, etc.) for displaying/presenting information to a user, such as an image and/or avatar associated with the user, image data depicting the placement of one or more transducer arrays on the surface (skin) of a user, image data depicting optimized and/or recommended areas for placement of one or more transducer arrays on the surface (skin) of the user, superimposed image data, and/or the like.

The user device 701 may include a communication module 704. The communication module 704 may enable the user device 701 to communicate with components of the system 700, such as the patient support module 706. The user device 701 may include an imaging module 703. The imaging module 703 may include one or more image capturing devices, such as one or more cameras that determine/capture image data (e.g., static/still images, dynamic/interactive images, video, etc.). The imaging module 703 may capture image data that provides a real-time and/or real-world representation of a user (e.g., a patient, a subject, etc.), such as a real-time and/or real-world representation of the user and/or a portion (e.g., head, torso, etc.) of the user's body. The user device 701 may include an image processing module 705. The image processing module 705 may process image data received from the imaging module 703 and determine one or more landmarks and/or one or more skin surface conditions from the image data. The image processing module 705 may use artificial intelligence and/or machine learning (e.g., a trained machine learning model, etc.), such as image/object recognition, to identify one or more landmarks and one or more skin surface conditions depicted by one or more images of the plurality of images included with the image data. The image processing module 705 may use one or more object identification and/or tracking algorithms to determine/detect the locations of the one or more landmarks and the one or more skin surface conditions.

The patient support module 706 may include a memory (system) 707. The memory 707 may include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory 707 may incorporate electronic, magnetic, optical, and/or other types of storage media. In an embodiment, the memory 707 may have a distributed architecture, where various components are situated remote from one another, but may be accessed by the processor 712. The memory 707 may include an EFG configuration application 708, a patient modeling application 710, imaging data 711, and a suitable operating system (O/S) 709. The operating system 709 may, essentially, control the execution of other computer programs, and provides scheduling, input-output control, file and data management, memory management, and communication control and related services.

The patient support module 706 may include a processor 712. The processor 712 may be a hardware device for executing software, particularly that stored in memory 707. The processor 712 may be any custom made or any commercially available processor, a central processing unit (CPU), an auxiliary processor among several processors associated with the patient support module 706, a semiconductor-based microprocessor (in the form of a microchip or chipset), or generally any device for executing software instructions. The patient support module 706 may include I/O interfaces 713 used to receive user input from and/or for providing system output to one or more devices or components, such as a user device 701. The I/O interfaces 713 may include, for example, a serial port, a parallel port, a Small Computer System Interface (SCSI), an IR interface, an RF interface, and/or a universal serial bus (USB) interface. A network interface 714 may be used to transmit and receive data/information from the patient support module 706.

The patient support module 706 may include an image processing module 715. The image processing module 715 may process image data received from the user device 701 (e.g., the imaging module 703, etc.). The image processing module 715 may determine one or more landmarks from the image data.

The patient support module 706 may include an image registration module 716. The image registration module 716 may register the 3D coordinates associated with the anatomical coordinate system (e.g., the transformed 3D points from the image data) to a 3D transducer array layout map. For example, the image registration module 716 may determine coordinates of the various landmarks indicated by image data that have been transformed into the anatomical coordinate system. The image registration module 716 may determine that the transformed coordinates of the various landmarks indicated by image data (e.g., the transformed 3D points from the image data) correspond to the coordinates of one or more landmarks indicated by the 3D transducer array layout map. The registered image data may be provided to a graphics rendering module 717. The graphics rendering module 717 may generate graphic guides along with the registered image data. Graphic guides may include representations of one or more transducer arrays of a 3D transducer array layout map indicated at positions (e.g., optimized positions) on the user that avoid (e.g., do not overlap, etc.) one or more skin surface conditions. The registered image data and associated graphic guides may be provided to an image rendering module 718. The image rendering module 718 may use the registered image data and associated graphic guides to generate composite data. The composite data may include a representation of the portion of the subject's body, a representation of at least one skin surface condition, and a representation of at least one recommended location of the transducer arrays. The avatar mapping and rendering module 719 may send an avatar (e.g., data/information indicative of the avatar, etc.) to the user device 701 for display.

Figure 8:
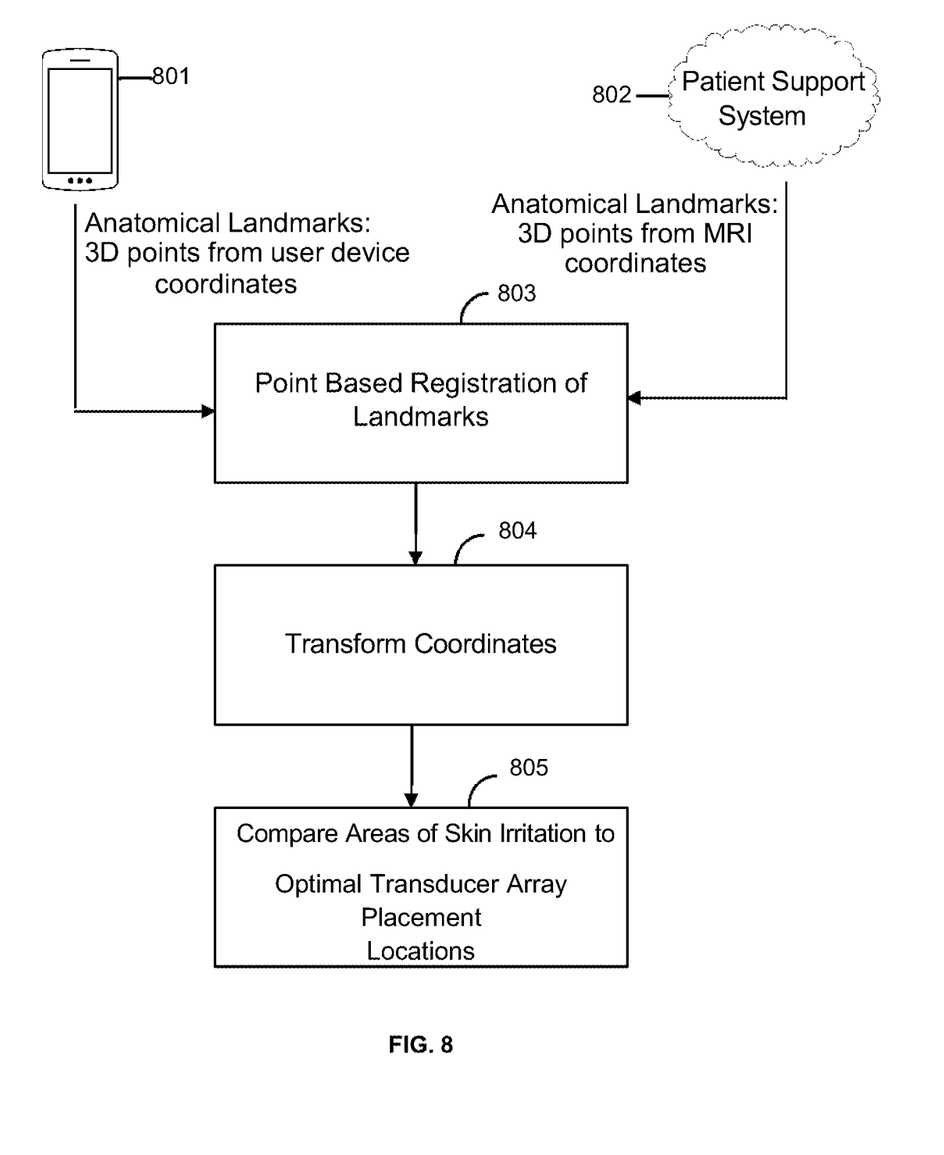
FIG. 8 depicts an example flowchart of a method for determining locations of transducer arrays.

FIG. 8 depicts an example flowchart of a method for determining locations of transducer arrays. The method enables points within 2D image data associated with a patient/subject's body to be transformed to points in 3D space.

At 801, a user device (etc., a smartphone, a mobile device, a computing device, etc.) may capture a plurality of images, from different vantage points and/or viewpoints, of a portion of a patient/subject's body that includes one or more landmarks and/or indicates one or more skin surface conditions, and/or any other dermatologic occurrence. The plurality of images may capture the one or more landmarks and/or the one or more skin surface conditions.

Points and/or coordinates associated with a coordinate system (e.g., 2D coordinate system, 3D coordinate system, etc.) relative to the plurality of images captured by the user device may be transformed to 3D points and/or coordinates (if they are not already 3D points and/or coordinates). For example, object recognition and/or the like may be used to determine/identify the one or more anatomical landmarks represented by the plurality of images. Points and/or coordinates associated with the one or more landmarks may be transformed to 3D points/coordinates. Identification information (e.g., a device identifier, a user identifier, user information, etc.) included with the data/information indicative of the 3D points/coordinates associated with the one or more transducer arrays and/or one or more landmarks may also be sent to the computing device and/or system (e.g., the patient support module 706).

At 802, the computing device and/or patient support system may use the identification information to determine medical imaging data, such as MRI data, associated with the patient/subject. The MRI data have been used for TTFields therapy/treatment planning for the patient/subject. The MRI data may include a volumetric representation of the portion of a patient/subject's body. The MRI data may include 3D coordinates. Object recognition and/or the like may be used to determine anatomical landmarks within the MRI data that correspond to the anatomical landmarks from the plurality of images. 3D points and/or coordinates associated with anatomical landmarks within the MRI data that correspond to the anatomical landmarks from the plurality of images may be determined.

At 803, a point-based registration of the anatomical landmarks from the plurality of images and the corresponding anatomical landmarks within the MRI data may be performed. Any method may be used to register the 3D points and/or coordinates associated with the anatomical landmarks from the plurality of images to the 3D points and/or coordinates associated with anatomical landmarks within the MRI data.

At 804, based on the registration of the 3D points and/or coordinates associated with the anatomical landmarks from the plurality of images to the 3D points and/or coordinates associated with landmarks within the MRI, all coordinates associated with the coordinate system relative to the plurality of images captured by the user device may be transformed to the coordinates of the MRI data. As such, any object included within the plurality of images and/or determined/detected from the plurality of images, such as the one or more skin surface conditions, may be represented along with the volumetric representation of the portion of a patient/subject's body. Coordinates indicative of locations/positions where the one or more skin surface conditions actually are may be used to represent the one or more skin surface conditions along with the volumetric representation of the portion of a patient/subject's body. Coordinates indicative of the optimized (e.g., recommended) transducer array placement positions determined from previous analysis of the MRI data may be used to determine one or more placement positions for transducer arrays that avoid (e.g., do not overlap, etc.) the one or more skin surface conditions, and/or any other dermatologic occurrence, and/or adhere to a transducer array placement restriction. The optimized (e.g., recommended) transducer array placement positions may be represented (e.g., displayed) with the volumetric representation of the portion of a patient/subject's body.

At 805, the locations/positions where the one or more areas of skin irritation exist may be compared to the optimized (e.g., recommended) transducer array placement positions that avoid (e.g., do not overlap, etc.) the one or more skin surface conditions, and/or adhere to a transducer array placement restriction. For example, the one or more skin surface conditions may be displayed (e.g., superimposed, overlaid, etc.) with the optimized (e.g., recommended) transducer array placement positions to illustrate the avoidance. The one or more skin surface conditions may be displayed (e.g., superimposed, overlaid, etc.) with representations of transducer array patches, disks, and/or the like at the optimized (e.g., recommended) transducer array placement positions that avoid (e.g., do not overlap, etc.) the one or more skin surface conditions, and/or adhere to a transducer array placement restriction. The display may include an actual image and/or realistic depiction of the patient/subject and/or the portion of the patient/subject's body.

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A method for determining placement positions for transducer arrays on a subject's body for applying tumor treating fields, the method comprising:

determining, by a processor and based on two-dimensional (2D) image data associated with a portion of a subject's body, one or more landmarks and one or more skin surface conditions, wherein the 2D image data is based on an exterior view of the subject's body obtained by a user device;

determining, by the processor, a representation of the one or more landmarks and the one or more skin surface conditions in three-dimensional (3D) space based on the one or more landmarks and one or more skin surface conditions determined from the 2D image data;

determining, by the processor and based on the representation of the one or more landmarks, the one or more skin surface conditions in 3D space, and a tumor location in the subject's body, a plurality of placement positions for one or more transducer arrays on the subject's body for applying tumor treating fields to the tumor location in the subject's body;

determining, by the processor and based on the one or more skin surface conditions in 3D space, one or more recommended placement positions of the plurality of placement positions for the one or more transducer arrays; and outputting, by the processor, an indication of the one or more recommended placement positions for the one or more transducer arrays.

2. The method of claim 1, wherein two of the recommended placement positions differ by at least one of:
locations on the subject's body to place the one or more transducer arrays;
sizes of electrodes of the one or more transducer arrays;
shapes of the one or more transducer arrays; or
orientations of the one or more transducer arrays.

3. The method of claim 1, wherein two of the recommended placement positions differ by the transducer array rotated by 10 degrees to 20 degrees around a centroid of the transducer array when compared to each other.

4. The method of claim 1, wherein at least one of the recommended placement positions comprises cutting away a portion of a bandage of one of the transducer arrays of the recommended placement position.

5. The method of claim 1, wherein at least one of the recommended placement positions comprises removing an electrode or part of an electrode of one of the transducer arrays of the recommended placement position.

6. The method of claim 1, wherein the one or more transducer arrays of the one or more recommended placement positions do not overlap with the one or more skin surface conditions.

7. The method of claim 1, wherein each electrode of the one or more transducer arrays of the one or more recommended placement positions does not overlap with the one or more skin surface conditions.

8. The method of claim 1, wherein at least one electrode of the one or more transducer arrays of the one or more recommended placement positions partially overlaps with the one or more skin surface conditions.

9. The method of claim 1, further comprising:
determining and outputting, by the processor, a percentage of overlap between the one or more skin surface conditions and each of the one or more transducer arrays of the one or more recommended placement positions.

10. The method of claim 1, wherein determining the one or more recommended placement positions is further based on a calculated power density delivered to the tumor location in the subject's body for each of the plurality of placement positions.

11. The method of claim 1, wherein determining the one or more recommended placement positions comprises:
ranking, by the processor, the plurality of placement positions based on at least one of:
a calculated power density delivered to the tumor location in the subject's body for each placement position;
a percentage of overlap between the skin surface conditions and a bandage of each transducer array of each placement position; or
a percentage of overlap between the skin surface conditions and each electrode of each transducer array of each placement position, and determining, by the processor, the one or more recommended transducer placement positions based on the ranking.

12. The method of claim 1, wherein the one or more landmarks comprise at least one of: an anatomical landmark, a sticker, or a temporary tattoo, and
wherein the one or more skin surface conditions comprise at least one of: a skin irritation, a skin reaction, a scar tissue, a surgical site, or an area of medical device implantation.

13. The method of claim 1, wherein the 2D image data is based on a plurality of images obtained by the user device, wherein each image of the plurality of images is associated with a different vantage point relative to the portion of the subject's body.

14. The method of claim 1, wherein the transducer comprises a plurality of ceramic disks.

15. The method of claim 1, wherein the transducer comprises a polymer film.

16. A method for determining locations of transducer arrays on a subject's body for applying tumor treating fields, the method comprising:
receiving, by a processor, based on two-dimensional (2D) image data associated with a portion of a subject's body, an indication of one or more potential skin surface conditions on the subject's body, wherein the 2D image data is based on an exterior view of the subject's body obtained by a user device;
receiving, by the processor, an indication that the one or more potential skin surface conditions are associated with one or more skin surface conditions;
determining, by the processor and based on the 2D image data and the indication that the one or more potential skin surface conditions are associated with the one or more skin surface conditions, a representation of the one or more skin surface conditions in three-dimensional (3D) space;
determining, by the processor and based on the representation of the one or more skin surface conditions in 3D space and a tumor location in the subject's body, one or more recommended locations of transducer arrays on the subject's body for applying tumor treating fields to the tumor location in the subject's body; and
outputting, by the processor, the one or more recommended locations of transducer arrays on the subject's body for applying tumor treating fields.

17. The method of claim 16, wherein outputting the one or more recommended locations of the transducer arrays comprises:
sending composite data to the user device, wherein the composite data comprises a representation of the portion of the subject's body, a representation of at least one skin surface condition, and a representation of at least one recommended location of the transducer arrays.

18. The method of claim 16, wherein determining the one or more recommended locations of the transducer arrays is further based on a transducer placement restriction, the transducer placement restriction restricting the one or more recommended locations based on overlap of the transducer arrays with the one or more skin surface conditions.

19. The method of claim 18, wherein the transducer placement restriction includes a threshold of overlapping between the transducer arrays and the one or more skin surface conditions.

20. A method for determining locations of transducer arrays on a subject's body for applying tumor treating fields, the method comprising:
- generating, by a processor and based on two-dimensional (2D) image data of a portion of the subject's body, a three-dimensional (3D) model of the portion of the subject's body, wherein the 3D model comprises one or more landmarks of the subject's body and one or more skin surface conditions of the subject's body, wherein the 2D image data is based on an exterior view of the subject's body obtained by a user device;
- determining, by the processor and based on the 3D model and a tumor location in the subject's body, one or more recommended locations of transducer arrays, wherein the one or more recommended locations of transducer arrays are determined based on an amount of overlap with the one or more skin surface conditions; and
- outputting, by the processor, the one or more recommended locations of transducer arrays for applying tumor treating fields to the tumor location in the subject's body.

* * * * *